US005672509A

United States Patent [19]
Fisher

[11] Patent Number: 5,672,509
[45] Date of Patent: Sep. 30, 1997

[54] HPDE IV-C: A HUMAN PHOSPHODIESTERASE IV ISOZYME

[75] Inventor: Douglas A. Fisher, Mystic, Conn.

[73] Assignee: Pfizer Inc., New York, N.Y.

[21] Appl. No.: 286,856

[22] Filed: Aug. 5, 1994

Related U.S. Application Data

[63] Continuation-in-part of Ser. No. 112,815, Aug. 25, 1993, abandoned.

[51] Int. Cl.$^6$ .................. C12N 5/10; C12N 15/09; C12N 15/12; C07H 21/04
[52] U.S. Cl. .................. 435/325; 435/320.1; 435/91.1; 536/23.2
[58] Field of Search .................. 536/23.2, 24.3, 536/24.31, 23.5; 435/240.2, 320.1, 91.1, 6, 172.1, 172.3, 325

[56] References Cited

U.S. PATENT DOCUMENTS

| | | | |
|---|---|---|---|
| 5,501,969 | 3/1996 | Hastings et al. | 435/252.33 |
| 5,504,003 | 4/1996 | Li et al. | 435/365.1 |
| 5,527,896 | 6/1996 | Wigler et al. | 536/23.5 |

FOREIGN PATENT DOCUMENTS

| | | |
|---|---|---|
| WO 91/16457 | 10/1991 | WIPO . |
| WO 92/18541 | 10/1992 | WIPO . |

OTHER PUBLICATIONS

Obernolte et al., *Gene*, 129, 239–247 (1993).
Kurihara et al., *Biochem, Biophys. Res. Comm.*, 170 (3), 1074–1081 (1990).
Weishaar et al., *J. Med. Chem.*, 28 (5), 537–545 (1985).
Giembycz, M.A., *Biochem. Pharm.*, 43 (10) 2041–2051 (1992).
Davis et al., *Proc. Nat'l. Acad. Sci. U.S.A.*, 83, 9313–9317 (Dec., 1986).
Conti et al., *Proc. Nat'l. Acad. Sci. U.S.A.*, 86, 5325–5329 (Jul., 1989).
Livi et al., *Mol. Cell. Biol.*, 10 (6), 2678–2686 (Jun., 1990).
Livi et al., *J. Biol. Chem.*, 268 (9), 6470–6476 (Mar., 1993).
Davis et al., *J. Cyclic Nucleotide Research*, 5 (1), 65–74 (1979).
Frohman et al., *Technique—A Journal of Methods in Cell and Molecular Biology*, 1 (3), 165–170 (Dec., 1989).
Chomoczynski et al., *Analytical Biochem*, 162, 156–159 (1987).
Torphy et al., *Mol. Pharm.*, 37, 206–214 (1990).
Beavo et al., *TIPS Reviews*, 149–155 (1990).
Beavo, J., "Cyclic Nucleotide Phosphodiesterases: Structure, Regulation and Drug Action", pp. 3–15, edited by Beavo, J. and Housley, M.D., John Wiley and Sons, Ltd. (1990).
Lowe et al., *Drugs of the Future*, 17 (9), 799–807 (1992).
Colicelli et al., *Proc. Nat'l. Acad. Sci. U.S.A.*, 86, 3599–3603 (May, 1989).
Venter et al., *Nature*, 355, 632–634 (Feb., 1992).
Venter et al., *Nature Genetics*, 4, 256–267 (Jul., 1993).
Davis et al., *Proc. Nat'l. Acad. Sci. U.S.A.*, 86, 3604–3608 (May, 1989).
Bolger et al., *Mol. Cell. Biol.*, 35, 1658 (1993).

*Primary Examiner*—George G. Elliott
*Assistant Examiner*—Thomas G. Larson
*Attorney, Agent, or Firm*—Peter C. Richrdson; Gregg C. Benson; Robert F. Sheyka

[57] ABSTRACT

This invention relates to a novel nucleic acid sequence encoding a novel human phosphodiesterase IV (hPDE IV) isozyme. It also relates to a polypeptide encoded by such sequence.

This invention also relates to an assay method for detecting the presence of such novel isozyme in human cells, and to a method of identifying compounds or other substances that inhibit or modify the activity of such isozyme.

4 Claims, 3 Drawing Sheets

FIG. 2A

```
-270  AGATCTCATGGTCACACAGGCACTCGGGGAACAGATCTGGGTCCAGGAGTCCTCGGTGGCCCCGTGGGAACAGTTTCAGGGT  -181

-39                                                         *  L  P  R  L  P  E  D  T
-180  CCAGATGAAGAGACGAAGTCGCGAGAGGGCGTGGGGTTGGGCAGGCCCCCTGAGCGGGGGGGTTGGGCAGGCCCCTGACTGCCTCGGCTCCCAG AGGACACG  -91

-30   G  Q  K  L  A  L  E  T  L  D  E  L  D  W  C  L  D  Q  L  E  T  L  Q  T  R  H  S  V  G  E  -1
-90   GGGCAGAAGCTGGCATTGGAGACGCTGGACGAGCTGGACTGGTGCCTGGATCAGTTGGAGACGCTGCAGACCGGCACTCGGTGTCGAGTAC  -1

1    M  A  S  N  K  P  K  R  I  L  N  R  E  L  T  H  L  S  G  T  S  R  S  G  N  Q  V  S  E  Y   30
 1    ATGGCCTCCAACAAGCCTAAGCGGATCCTGAACCGGGAGTTGACCCACCTGTCCGGAACCAGCGCTCGGAAACCAGCAGTTCCCGATCAGT   90

31   I  S  R  T  F  L  D  Q  Q  T  E  V  E  L  P  K  V  T  A  E  E  A  P  Q  P  M  S  R  I  S   60
 91   ATCTCCCGGACCTTCCTGGACCAGCAGACAGAAGTGGAGCTGCCCAAGGTGACTGCTGAAGAGGCCCCACAGCCCATGTCCCGGATCAGT  180

61   G  L  H  G  L  C  H  S  A  S  L  S  S  A  T  V  P  R  F  G  V  Q  T  D  Q  E  E  Q  L  A   90
181   GGCCTACATGGGCTCTGCCACAGTGCCAGCCTCTCTCAGCCTGCCACTGTCCACGCTTTGGGGTCCAGACTGACCAGGAGGAGCAACTGGCC  270

91   K  E  L  E  D  T  N  K  W  G  L  D  V  F  K  V  A  E  L  S  G  N  R  P  L  T  A  I  I  F  120
271   AAGGAGCTAGAAGACACCAACAAGTGGGGACTTGATGTGTTCAAGGTGGCGGAGCTAAGTGGGAACCGGCCCCTCACAGCTATCATATTC  360

121   S  I  F  Q  E  R  D  L  L  K  T  F  Q  I  P  A  D  T  L  A  T  Y  L  L  M  L  E  G  H  Y  150
361   AGCATTTTTCAGGAGCGGGACCTGCTGAAGACATTCCAGATCCCAGCAGACACACTGGCCACCTACCTGCTGATGCTGGAGGGTCACTAC  450

151   H  A  N  V  A  Y  H  N  S  L  H  A  A  D  V  A  Q  S  T  H  V  L  L  A  T  P  A  L  E  A  180
451   CACGCCAATGTGGCCTACCACAACAGCCTACATGCCGCCGACGTGGCCCAGTCCACCCATGTCCTGCTGGCTACGCCCGCCCTCGAGGCT  540

181   V  F  T  D  L  E  I  L  A  A  L  F  A  S  A  I  H  D  V  D  H  P  G  V  S  N  Q  F  L  I  210
541   GTGTTCACAGACTTGGAAATCCTGGCTGCCCTCTTTGCAAGCGCCATCCACGACGTGGACCATCCTGGGGTCTCCAACCAGTTTCTGATT  630

211   N  T  N  S  E  L  A  L  M  Y  N  D  A  S  V  L  E  N  H  H  L  A  V  G  F  K  L  L  Q  A  240
631   AACACCAACTCAGAGCTGGCGCTTATGTACAACGACGCCTCAGTGCTGGAGAATCATCACCTGGCTGTGGGCTTCAAGCTGCTGCAGGCAGCA  720
```

FIG. 2B

```
241  E  N  C  D  I  F  Q  N  L  S  A  K  Q  R  L  S  L  R  R  M  V  I  D  M  V  L  A  T  D  M                    270
721  GAGAACTGCGATATCTTCCAGAACCTCAGCGCCAAGCAGCGACTGAGTCTGCGCAGGATGGTCATTGACATGGTCTGGCCACAGACATG                    810

271  S  K  H  M  N  L  L  A  D  L  K  T  M  V  E  T  K  K  V  T  S  L  G  V  L  L  L  D  N  Y                    300
811  TCCAAACACATGAACCTCCTGGCCGACCTCAAGACCATGGTGGAGACCAAGAAGGTGACAAGCCTCGGTGTCCTCCTGGACAACTAT                      900

301  S  D  R  I  Q  V  L  Q  N  L  V  H  C  A  D  L  S  N  P  T  K  P  L  P  L  Y  R  Q  W  T                    330
901  TCCGACCGAATCCAGGTCTTGCAGAACCTGGTGCACTGTGCTGATCTGAGCAACCCGACCAAACCGCTGCCCCTGTACCGCCAGTGGACG                    990

331  D  R  I  M  A  E  F  F  Q  Q  G  D  R  E  R  E  S  G  L  D  I  S  P  M  C  D  K  H  T  A                    360
991  GACCGCATCATGGCCGAGTTCTTCCAGCAGGGAGACCGCGAGCGTGAGTCGGGCCTGGACATCAGTCCCATGTGTGACAAGCATACGGCC                    1080

361  S  V  E  K  S  Q  V  G  F  I  D  Y  I  A  H  P  L  W  E  T  W  A  D  L  V  H  P  D  A  Q                    390
1081 TCAGTGGAGAAGTCCCAGGTGGGTTTCATTGACTACATTGCTCACCCACTGTGGGAGACTTGGGCTGACCTGGTCCACCCAGATGCACAG                    1170

391  D  L  L  D  T  L  E  D  N  R  E  W  Y  Q  S  K  I  P  R  S  P  S  D  L  T  N  P  E  R  D                    420
1171 GACCTGCTGGACACGCTGGAGGACAATCGAGAGTGGTACCAGAGCAAGATCCCCCGAAGTCCCTCAGACCTCACCAACCCCGAGCGGGAC                    1260

421  G  P  D  R  F  Q  F  E  L  T  L  E  E  A  E  E  E  D  E  E  G  G  A  G  G  A  A  G  A  C  T  T  T  A        450
1261 GGGCCCTGACAGATTCCAGTTTGAACTGACTCTGGAGGAGGCAGAGGAAGAGGATGAGGAGGAAGAGAGGGAAGAGACAGCTTTA                         1350

451  A  K  E  A  L  E  L  P  D  T  E  L  L  S  P  E  A  G  P  D  P  G  D  L  P  L  D  N  Q  R                    480
1351 GCCAAAGAGGCCCTTGAGTTGCCTGACACTGAACTCCTGTCCCCTGAAGCCGGCCCAGACCCTGGGGACTTACCCCCTCGACAACCAGAGG                   1440

481  T  *                                                                                                         481
1441 ACTTAGGGCCAGCCCTGCCGTGAACTGCAGGGCCAATGATGGTAAAGCCCTTTGGCTCTCTTGGCCAGGCAGACTTTCCAGGAAGAGGCTCCA                 1530
1531 TGTGGCTCCTGCTTCACTTTCCCACCCATTTAGGGAGACAATCAAGCTCTTAGTTATAGGTGGCTCCCAGGTCTAATTGGAGGCACCTG                     1620
1621 GCTGGGGTCCACTCTGACCTCTAAGAGCTCTTAAGGGCAGCCTCTGGTCTTTCTCCTGGCTTC                                                1710
1711 TATCCCTGTGAGGAGAGGTGCTGTCTGCTGGAGCCTCTAGTCCACCCTCTCACTCTTGAGTCACATCTGTCACTTAATTATT                            1800
1801 TCCTTCTTTATCAAATATTTA                                                                                         1821
```

HPDE IV-C: A HUMAN PHOSPHODIESTERASE IV ISOZYME

BACKGROUND OF THE INVENTION

This application is a continuation-in-part of U.S. patent application Ser. No. 08/112,815, which was filed on Aug. 25, 1993, now abandoned. U.S. Ser. No. 08/112,815 is incorporated herein by reference in its entirety.

This invention relates to novel nucleic acid sequences encoding a novel human phosphodiesterase IV (hPDE IV) isozyme.

Cyclic nucleotide phosphodiesterases (PDEs) are a family of enzymes that catalyze the degradation cyclic nucleotides. Cyclic nucleotides, particularly cAMP, are important intracellular second messengers, and PDEs are one cellular component that regulates their concentration. In recent years, five PDE enzymes (PDE I–PDE V), as well as many subtypes of these enzymes, have been defined based on substrate affinity and cofactor requirements (Beavo JA and Reifsnyder DH, *Trends Pharmacol. Sci.* 11:150 [1990]; Beavo J, In: *Cyclic Nucleotide Phosphodiesterases: Structure, Regulation and Drug Action.*, Beavo J and Housley MD (Eds.). Wiley: Chichester, pp. 3–15 [1990]).

Theophylline, a general PDE inhibitor, has been widely used in the treatment of asthma. It has been speculated that selective inhibitors of PDE isozymes and their subtypes (particularly the cAMP-specific PDE IV) will lead to more effective therapy with fewer side effects (for reviews, see Wieshaar RE et al, *J. Med. Chem.*, 28:537 [1985]and Giembycz MA, *Biochem. Pharm.*, 43:2041 [1992], Lowe JA and Chang JB, *Drugs of the Future*, 17:799–807 [1992]). However, even PDE IV selective drugs such as rolipram suffer from emetic side effects that limit their use. An even more selective approach is to inhibit individual subtypes of PDE IV, each one of which is expected to have its own tissue distribution. If the PDE IV isozyme responsible for efficacy is different from that causing side effects, an isozyme selective drug could separate therapeutic and side effects. The cloning and expression of the human PDE IVs would greatly aid the discovery of isozyme-selective inhibitors by providing purified isoenzymes to incorporate into drug assays.

Mammalian PDE IV, the homologue of the Drosophila Dunce gene (Chen CN et al., *Proc. Nat. Acad. Sci.* (USA) 83:9313 [1986]), is known to have four isoforms in the rat (Swinnen JV et al., *Proc. Nat. Acad. Sci.* (USA) 86:5325 [1989]). The cloning of one human isoform of PDE IV from monocytes was reported in 1990 (Livi GP et al., *Mol. Cell. Bio.*, 10:2678 [1990]). From Southern blot data, the authors concluded that this enzyme was probably the only PDE IV gene in humans, with the possible exception of one other isozyme. The same group has published the sequence of a second human isoform isolated from brain that they designate hPDE IV-B to distinguish it from the monocyte form, which they designate as hPDE IV-A (McLaughlin MM et al, *J. Biol. Chem.* 268:6470 [1993]). We have independently cloned three splice variants of hPDE IV-B, which we have designated hPDE IV-B1, −B2, and −B3. The sequence reported by McLaughlin et al., is nearly identical to our hPDE IV-B2 sequence, while the −B1 and −B3 sequences encode functional PDE IV enzymes with different N-terminal amino acid sequences.

The nucleic acid sequences encoding hPDE IV-B1, hPDE IV-B2 and hPDE IV-B3 are described and claimed in U.S. patent application Ser. No. 08/075,450, which was filed on Jun. 11, 1993. This application is incorporated herein by reference in its entirety.

This invention relates to nucleic acid sequences encoding a novel human PDE IV isozyme, which we designate as hPDE IV-C. Such a novel human PDE IV DNA sequence and its encoded peptide may be used to screen for drugs that are selective for the human PDE IV-C isozyme or used to exclude activity against hPDE IV-C to find agents selective for other hPDE IV isozymes. Such novel DNA sequence may also be used in assays to detect the presence of the human PDE IV-C isozyme in human cells, thus providing information regarding the tissue distribution of this isozyme and its biological relevance with respect to particular disease states.

U.S. application Ser. No. 08/122,815, of which this application is a continuation-in-part, claims a hPDE IV-C cDNA sequence containing 1296 base pairs, which encode the C-terminal 306 amino acids of hPDE IV-C. Subsequent to the filing of U.S. application Ser. No. 08/122,815, referred to above, a fragment of the hPDE IV-C cDNA sequence claimed in that application was published by Bolger et. al., *Mol. Cell. Biol.*, 13, 1658 (1993). The fragment published by Bolger et al. is smaller than the sequence claimed in U.S. Ser. No. 08/112,815, and does not encode a large enough portion of the coding region to produce a functional protein. The Bolger sequence constitutes bases 961 to 2091 of SEQUENCE ID NO. 1 of the present invention, and the sequence claimed in U.S. Ser. No. 08/122,815 constitutes bases 796–2091 of SEQUENCE ID NO. 1 of the present invention. SEQUENCE ID NO. 1 of this invention represents a full length hPDE IV-C cDNA sequence which encodes a catalytically active protein that can be used to screen for isozyme selective drugs.

The following abbreviations are used throughout this patent:

| | |
|---|---|
| bp | base pair(s) |
| cAMP | cyclic adenosine 3′,5′-monophosphate |
| dNTP | 2′-deoxynucleoside-5′-triphosphate |
| dATP | 2′-deoxyadenosine-5′-triphosphate |
| dCTP | 2′-deoxycytidine-5′-triphosphate |
| dGTP | 2′-deoxyguanine-5′-triphosphate |
| DTTP | 2′-deoxythymidine-5′-triphosphate |
| hPDE IV-A | human monocute PDE IV |
| hPDE IV-B | human brain PDE IV |
| hPDE IV-B1 | human brain PDE IV, splice variant 1 |
| hPDE IV-B2 | human brain PDE IV, splice variant 2 |
| hPDE IV-B3 | human brain PDE IV, splice variant 3 |
| hPDE IV-C | human tdstis PDE IV |
| kb | kilobase(s) |
| PCR | polymerase chain reaction |
| PDE | cyclic nucleotide phosphodiesterase |
| PDF I | $Ca^{2+}$/Calmodulin-dependent PDE |
| PDE II | cGMP stimulated PDE |
| PDE III | cGMP inhibited PDE |
| PDE IV | high affinity cAMP-specific PDE |
| PDE V | cGMP specific PDE |
| RACE | Rapid Amplification of cDNA Ends |
| RT | avian myeloblastosis virus (AMV) reverse transcriptase |
| RT-PCR | PCR of RT-transcribed mRNA |
| SSC | 1X SSC = 0.15 M NaCl, 0.015 $Na_3$ citrate pH 7.0 |

The nucleotides and amino acids represented in the various sequences contained herein have their usual single letter designations used routinely in the art.

SUMMARY OF THE INVENTION

This invention relates to the full length cDNA sequence of the novel human PDE IV isozyme hPDE IV-C. More specifically, it relates to DNA segments comprising the DNA sequence of SEQUENCE ID NO. 1, as defined below, or an alleleic variation of such sequence. It also relates to polypeptides produced by expression in a host cell into which has been incorporated the foregoing DNA sequence or an alleleic variation thereof.

This invention also relates to an isolated polypeptide containing the amino acid sequence of SEQUENCE ID NO. 2 or SEQUENCE ID NO. 3.

This invention also relates to recombinant DNA comprising the DNA sequence of SEQUENCE ID NO. 1, or an alleleic variation thereof.

This invention also relates to an isolated DNA segment comprising the genomic promoter region that regulates transcription or translation of the DNA sequence of SEQUENCE ID NO. 1, or an allelic variation thereof.

This invention also relates to an assay method for detecting the presence of hPDE IV-C in human cells comprising: (a) performing a reverse transcriptase-polymerase chain reaction on total RNA from such cells using a pair of polymerase chain reaction primers that are specific for hPDE IV-C, as determined from the DNA sequence of SEQUENCE ID NO. 1, or an allelic variation thereof; and (b) assaying the appearance of a appropriately sized PCR fragment by agarose gel electrophoresis.

This invention also relates to a method of identifying compounds or other substances that inhibit or modify the activity of hPDE IV-C, comprising measuring the activity of hPDE IV-C in: (a) a cell line into which has been incorporated recombinant DNA comprising the DNA sequence of SEQUENCE ID NO. 1, or an alleleic variation thereof, or (b) a cell population or cell line that naturally selectively expresses hPDE IV-C, as determined by the assay method described above.

This invention also relates to an isolated DNA segment comprising a DNA sequence that is a subset of SEQUENCE ID NO. 1, or an alleleic variation thereof, and that is capable of hybridizing to SEQUENCE ID NO. 1, or an alleleic variation thereof, when used as a probe, or of amplifying all or part of such sequence when used as a polymerase chain reaction primer.

As used herein, the term "functionally equivalent DNA segment" refers to a DNA segment that encodes a polypeptide having an activity that is substantially the same as the activity of the polypeptide encoded by the DNA to which such segment is said to be functionally equivalent.

As used herein, the term "subset of a DNA sequence" refers to a nucleotide sequence that is contained in an represents part, but not all of such DNA sequence, and is sufficient to render it specific to such sequence when used as a PCR primer and render it capable of hybridizing to such sequence when used as a probe at high stringency.

As used herein, the term "functionally equivalent polypeptide" refers to a polypeptide that has substantially the same activity as the polypeptide to which it is said to be functionally equivalent.

As used herein, the term "subset of a polypeptide" refers to a peptide sequence that is contained in and represents part, but not all of such polypeptide.

BRIEF DESCRIPTION OF THE DRAWINGS

FIG. 2. hPDE IV-C DNA Sequence and Translated Amino Acid Sequence. The translated amino acids of hPDE IV-C are indicated above the cDNA sequence. The stop codon (bp 1,444–1,446) is indicated by "Trm". Positive numbering begins at the putative start codon with negative numbering (cDNA and amino acids) back into the 5' UTR. A putative splice junction is indicated by an arrow at nucleotide (nt) −99, the homologous position seen in hPDE IV-B. An in frame stop codon (nt −117 to −115) in the 5' UTR is noted by an asterisk. The sequence claimed in U.S. Ser. No. 08/122,815 begins at nt 526 (796 in SEQUENCE ID NO. 1), amino acid (AA) 176, and continues to the end of the sequence. There are three changes in the nucleotide sequence from the parent case (U.S. Ser. No. 08/112,815). These are the following (using the numbering from SEQ. ID NO. 1 of U.S. Ser. No. 08/112,815): nt 3 changes from C to G, nt 7 changes from T to C, and nt 438 changes from A to G. One of these (nt 7) changes an amino acid, so amino acid 3 of SEQ. ID NO. 2 of U.S. Ser. No. 08/122, 815 is changed from Phe to Leu. The corresponding positions of these changes in the present application are: (SEQUENCE ID NO. 1-nt 798, 802, and 1,233; SEQUENCE ID NO. 2-AA 178; SEQUENCE ID NO. 3-AA 203).

DETAILED DESCRIPTION OF THE INVENTION

Figure 1:
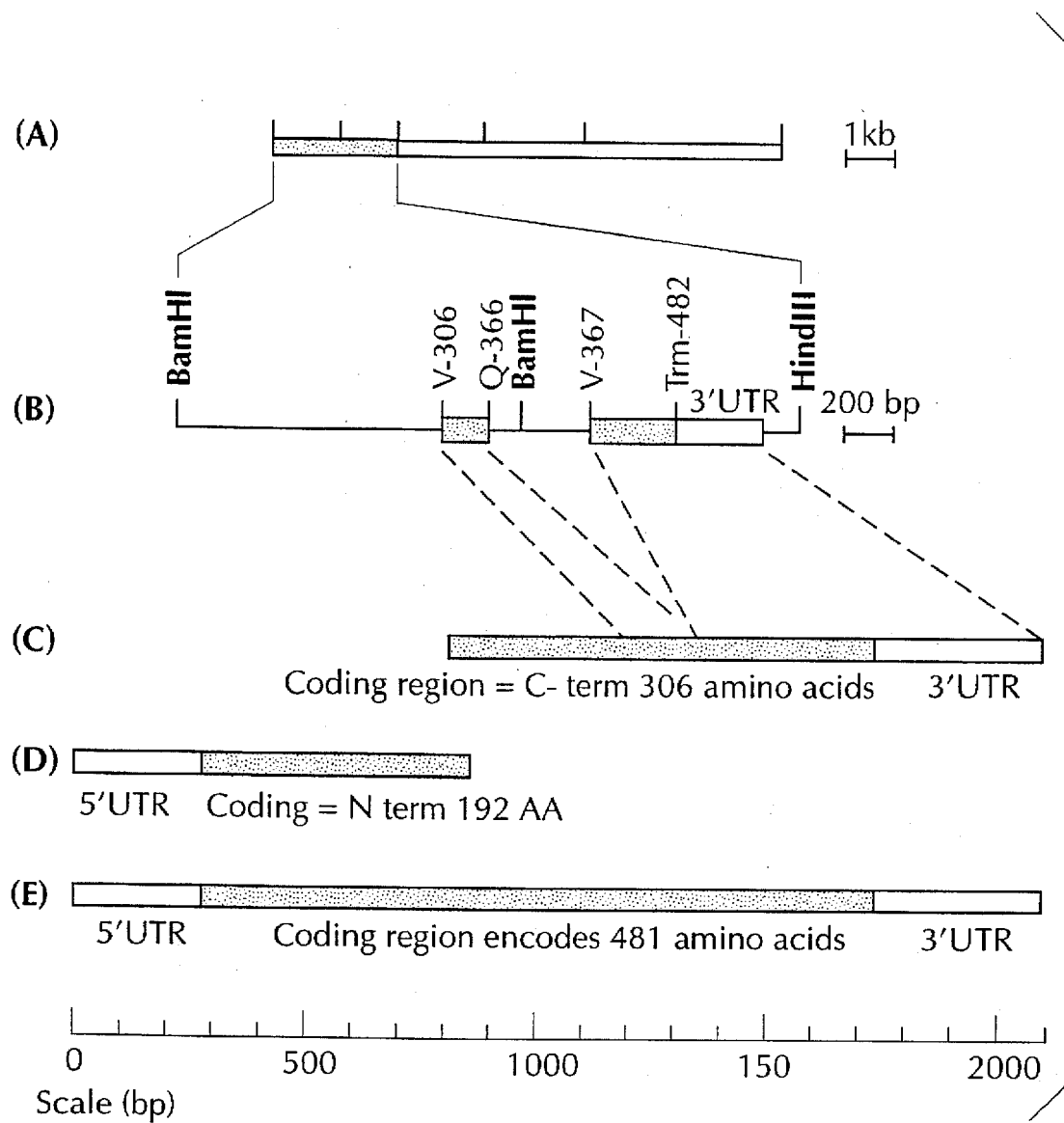
FIG. 1, parts A–E. hPDE IV-C Restriction Map and Clone Diagram. (A) Partial restriction map of the approximately 11 kb insert of clone λC2.1, the genomic clone containing two exons of hPDE IV-C. The region hybridizing with the hPDE IV-A,B probes is indicated as a shaded box. (B) Diagram of the 2.7 kb of DNA indicated by a shaded box in (A). Protein coding exons are indicated by solid boxes, while the 3' untranslated region (3'UTR) is indicated as an open box. The amino acids at the intron exon boundaries (numbering as in FIG. 2) are shown above the solid boxes. The 3'UTR is only indicated as far as was confirmed by the cDNA clone of hPDE IV-C, T.29. It is not known if the 3'UTR extends further in the 3' direction on λC2.1. (C) Diagram of the insert of cDNA clone T.29, a cDNA clone containing a partial hPDE IV sequence. Solid boxes indicated protein coding regions, while open boxes indicate 3'UTR. Dashed lines from (B) show the regions in (C) corresponding to the exons in (B). (D) Diagram of the region cloned by 5' RACE, which encodes the N-terminal 192 amino acids (solid box) and 270 bp of 5' untranslated region (open box). (E) Diagram of the assembled full length cDNA sequence encoding a 481 amino acid polypeptide. Scale at the bottom relates to (C),(D), and (E). Scales for (A) and (B) are to the right of each diagram.

The procedures by which the DNA sequence encoding the novel isozyme, hPDE IV-C, was identified and isolated are described below.

Discovery of hPDE IV-C by Isolation of a Genomic Clone:

A human genomic library was screened as described in Materials and Methods, and clone λC2.1 was isolated. A partial restriction map of the approximately 11 kb insert is shown in FIG. 1A. Only the region indicated by the shaded box in FIG. 1A hybridized to the hPDE IV-A,B probe, and the DNA sequence of this region was determined.

Two exons with homology (85–95%) to known PDE IV genes were found (FIG. 1B, solid boxes) in the region sequenced. This level of homology clearly places this gene in the PDE IV gene family. Since this gene is not identical to either of the known human PDE IV genes, we conclude that this is a novel human PDE IV gene, and designate it as hPDE IV-C. Together, these two exons of hPDEE IV-C would encode the C-terminal 176 amino acids of a hPDE IV protein. The exact extent of the 3' untranslated region is unclear, because this region is not conserved in homologous genes and because it is possible that there is an intron in the 3'UTR. The 176 amino acids extend 94 amino acids into the highly conserved approximately 270 amino acid catalytic domain of PDE IV (Swinnen JV et al, *Proc. Nat. Acad. Sci.* (USA) 86:5325 [1989]).

Isolation of a cDNA Clone for hPDE IV-C

A human testis cDNA library was screened as described in Materials and Methods, and cDNA clone T.29 was obtained. The DNA sequence of the insert was determined, and is shown in SEQUENCE ID NO. 1 and in FIG. 2, with the exception of 33 bp of a likely cloning artifact at the 5' end. A diagram of clone T.29 and its relationship to the two exons determined for clone λC2.1 are shown in FIG. 1C. The 3' 906 bp (bp 1186–2091 in SEQUENCE ID NO. 1) of clone T.29 are identical to the sequence determined from clone λC2.1. The sequence of T.29 extends the sequence of hPDE IV-C another 390 bp in the 5' direction (bp 796–1185 in SEQUENCE ID NO.1, FIG. 2), adding 130 amino acids to the amino acid sequence, or 224 amino acids into the approximately 270 amino acid catalytic domain. This means that T.29 is not full length and encodes the C-terminal 306 amino acids of hPDE IV-C.

Since no polyA tract was found at the 3' end of clone T.29, and since the cDNA library was made by a combination of oligo dT and random priming, we do not believe that the 3' untranslated region is full length. However, this is probably of no functional significance with respect to producing a recombinant PDE since this region does not encode protein.

Completion of a full length cDNA using 5' RACE

5' RACE was performed as described below in Materials and Methods, section (e). The hPDE IV-C cDNA sequence was extended farther 5', as shown in FIG. 1D. The combined cDNA sequence (FIG. 1E) contains a full length cDNA of one splice variant. The predicted amino acid sequence is 481 amino acids in length. Clearly, there are other splice variants, because the region upstream of the start codon (AA's –1 to –33 in FIG. 2) has homology to other PDE IV genes, and this similarity terminates precisely at the point homologous to a splice junction in hPDE IV-B (shown by an arrow in FIG. 2). For nucleotides –1 to –98 to be conserved in evolution, they must be protein codins in another splice variant, so other N-terminally extended variants must exist. Such variants have not yet been cloned, but further 5' RACE experiments in multiple tissues could elucidate these variants.

The translated amino acid sequence of hPDE IV-C is most similar to the rat PDE IV isozyme PDEI (Swinnen JV et al., [1989]) with 92.5% identity in the 267 amino acids of the catalytic domain. The rat PDE 2, 3 and 4 isozymes referred to in that reference have 88.0%, 88.4%, and 85.8% amino acid identity, respectively, over the same region. The present inventor tentatively identifies hPDE IV-C as the human homolog of the rat PDE IV isozyme PDEI. The other human isozymes are approximately as different from hPDE IV-C as hPDE IV-C is from the rat isozymes; with hPDE IV-A and hPDE IV-B sharing 88.8% and 86.1% amino acid identity in the catalytic domain.

hPDE IV-C is Expressed in Human Brainstem

The fact that a clone for hPDE IV-C was isolated from a testis cDNA library shows that this gene is expressed in the testis and processed into polyA +mRNA. To further show that hPDE IV-C is expressed, we analyzed human tissues by RT-PCR using the methods described in Materials and Methods and the hPDE IV-C specific PCR primer pairs described below in Assays. hPDE IV-C is expressed in a number of tissues, with the highest levels occurring in the brain.

Expression Cloninfi of hPDE IV-C

The hPDE IV-C cDNA sequence was cloned into pcDNA3 (Invitrogen) for expression in mammalian cells. Since the region encoding 33 amino acids upstream of the putative start codon is likely used in other splice variants, we added some of these amino acids in making an expression construct. In hPDE IV-B3 (Fisher, D. A. and Robbins, M. D., U.S. Ser. No. 08/075,450, referred to above), a methionine at the homologous position to leucine –25 serves as a functional start codon that makes a catalytically active protein. Therefore, we mutated leu –25 into a met start codon, added translation initiation sequences (Kozak, M., *Nucleic Acids Res.*, 15:8125 [1987]), and cloned into pcDNA3 to produce the plasmid pc3-hPDE IV-C. Because of the addition of a KpnI restriction site to the sequence, the first three amino acids are altered. The expression construct is predicted to make the polypeptide shown in SEQUENCE ID NO. 3.

After transient transfection into 293 cells by methods familiar to those skilled in the art (calcium phosphate precipitation, electroporation, etc.) the expression construct leads to the synthesis of catalytically active hPDE IV-C, as evidenced by a 3–10× increase in PDE IV enzymatic activity over pcDNA3 (vector) transfected controls. Therefore, the disclosed sequence is sufficient to produce functional hPDE IV-C. The expression construct pc3-hPDE IV-C has been deposited with the ATCC (see below).

Deposits

The cDNA expression clone containing the hPDE IV-C sequence, pc3-hPDE IV-C, has been deposited with the American Type Culture Collection, Rockville, Md. U.S.A. (ATCC) and assigned the accession number ATCC 69609.

Assays

Using the DNA sequence of hPDE IV-C, hPDE IV-B, and hPDE IV-A, one skilled in the art could make a large number of isoenzyme specific PCR primer pairs. Specificity is achieved by choosing primers that are an exact match for the desired isozyme but which have enough mismatches in the homologous region of the undesired isozymes to render them incapable of amplifying a DNA fragment from mRNA from those isozymes in an RT-PCR assay. We have made and tested the following hPDE IV-C, hPDE IV-B, and hPDE IV-A specific primer pairs. The primers 5'C (5'-GGAGAAGTCCCAGGTGGGTTT-3') SEQ ID No:4 and 3'C (5'-TCTGGTTGTCGAGGGGTAAGT-3') SEQ ID NO:5 are a pair of 21-mers that specifically amplify a 350 bp fragment of hPDE IV-C. The primers 5'B (5'-CGAAGAAAGTTACAAGTTC-3') SEQ ID NO:6 and 3'B (5'-AACCTGGGATTTTTCCACA-3') SEQ ID NO:7 are a pair of 19-mers that specifically amplify a 245 bp fragment from hPDE IV-B. The primers 5'A (5'-CACCTGCATCATGTACATG-3') SEQ ID NO:8 and 3'A (5'-TCCCGGTTGTCCTCCAAAG-3') SEQ ID NO:9 are 19-mers that amplify an 850 bp fragment specifically from hPDE IV-A. Using these primers, one can sensitively assay the presence of these three isozymes in any tissue from which total RNA can be isolated (e.g., by the method of Chomcynski P and N Sacchi, *Anal. Biochem.* 162:156 [1987]) by performing an RT-PCR reaction on such RNA using the specific primers and then assaying the amount of the appropriately sized DNA PCR product by agarose gel electrophoresis. The RT-PCR conditions are identical to those described in Materials and Methods.

The claimed DNA sequences of this invention can be reproduced by one skilled in the art by either PCR amplification from brainstem RNA using PCR primers designed from the sequences, or by obtaining the described cDNA clone directly from ATCC. The promoter regions can be isolated from a genomic library, using the claimed sequences as probes.

Utility of the Invention

A general utility of the novel human PDE IV genes and their encoded peptides is to allow screening for human PDE IV isozyme specific/selective drugs that may be improved therapeutics in the areas of asthma and inflammation. The cloned genes make it possible, by expression cloning methods familiar to those skilled in the art, to produce active, purified isoenzymes that can be used in PDE IV activity assays (e.g., Davis CW, and Daly JW, *J. Cyclic Nucleotide Res.* 5:65 [1979], Torphy TJ and Cielinski LB, *Mol. Pharm.* 37:206 [1990]) to measure the potency of inhibitors against individual isoenzymes.

Genomic sequences are also of utility in the context of drug discovery. It may be valuable to inhibit the mRNA transcription of a particular isoform rather than to inhibit its translated protein. This is particularly true with hPDE IV-B, since the different splice variants may be transcribed from different promoters. There is precedent for multiple promoters directing the transcription of a mouse brain 2',3'-cyclicnucleotide 3' phosphodiesterase (Kurihara T et al., *Biochem. Biophys. Res. Comm.* 170:1074 [1990]). This invention would provide the means for one skilled in the art to locate the promoter of hPDE IV-C. After isolating a full length cDNA clone using the hPDE IV-C sequence as a probe, screening of a human genomic library with the 5' cDNA sequences should allow isolation of genomic clones containing the promoter. Such promoters could then be linked to a convenient reporter gene such as firefly luciferase (de Wet JR et al., *Mol. Cell. Biol.* 7:725 [1987]), transfected into a mammalian cell line, and agents screened for that inhibit the activity of the promoter of interest while having minimal effect on other promoters.

Another utility of the invention is that the DNA sequences, once known, give the information needed to design assays to specifically detect each isoenzyme or splice variant. Isozyme-specific PCR primer pairs are but one example of an assay that depends completely on the knowledge of the specific DNA sequence of the isozyme or splice variant. Such an assay allows detection of mRNA for the isozyme to access the tissue distribution and biological relevance of each isozyme to a particular disease state. It also allows identification of cell lines that may naturally express only one isozyme—a discovery that might obviate the need to express recombinant genes. If specific hPDE IV isozymes are shown to associated with a particular disease state, the invention would be valuable in the design of diagnostic assays to detect the presence of isozyme mRNA.

Materials and Methods (a) Cells/Reagents

Human brainstem tissue was purchased from the International Institute for the Advancement of Medicine. Unless noted below, all restriction endonucleases and DNA modifying enzymes were from Boehringer-Mannheim.

(b) RT-PCR

Total RNA was isolated from human tissue as previously described (Chomcynski P and Sacchi N, *Anal. Biochem.* 162:156 [1987]). To prepare an 80 µl reverse transcriptase (RT) reaction, 4 ,µg total RNA and 4 µg random hexamer primers (Pharmacia/LKB) were heated to 90° C. for 5 min in 60 µl RNase free water. After chilling on ice, the reaction was brought to 80 µl and the following conditions by the addition of concentrated stocks: 1×RT buffer (50 mM Tris pH 8.3, 6 mM magnesium chloride ($MgCl_2$,) 40 mM potassium chloride (KCl); 1 mM each dATP, dGTP, dCTP, and dTTP; 1 mM dithiothreitol; 25 U/ml RNasin (Promega); and 900 U/ml AMV reverse transcriptase (RT). Incubate at 42° C. for 1 hour, then boil for 5 min to kill the RT.

A 50 µl PCR reaction was set up by using 3.25 µl of the above reaction mix. Final buffer conditions were (including carryover from RT): 10 mM Tris pH 8.3, 50 mM potassium chloride (KCl), 1.5 mM $MgCl_2$, 10 µg/ml bovine serum albumin, 2.5% (v/v) Formamide, 200 µM ea dNTP, 0.5 pmol/µl each degenerate primer, and 0.05 U/µl Amplitaq polymerase (Perkin Elmer). Amplification was done in a Perkin Elmer 9600 PCR thermocycler using the following parameters: Denature-94° C., 30 sec; Anneal-55° C., 30 sec, Polymerize-72° C., 60 sec. Amplify for 35 cycles.

(c) Library Screening $1\times10^6$ clones from a commercially available human genomic library (Clontech #HL1111j) were screened with a 308 bp PCR fragment of hPDE IV-A from the highly conserved PDE catalytic domain (bp 1069 to 1376 [amino acids 357–459] in Livi GP et al., [1990]) and the homologous fragment from hPDE IV-B. The screening conditions were as follows: 5×SSC, 5×Denhardts solution (1×Denhardt's=0.02% each of Ficoll, polyvinylpyrrolidone, and bovine serum albumin), 40% formamide, 0.5% sodium dodecyl sulfate, and 20 µg/ml herring sperm DNA. Probe concentration was $4\times10^5$ cpm/ml. The filters were hybridized at 42° C. for >16 hours, and then washed to a final stringency of 0.5×SSC at room temperature.

$1\times10^6$ clones from a human testis cDNA library (Clontech: HL1161a) were screened as for the genomic library, except the formamide concentration was 35%. The filters were washed to a final stringency of 0.5×SSC at room temperature.

(d) DNA Sequencing

All DNA sequencing was done using an ABI model 373A DNA sequencer on DNA fragments cloned into various pGEM vectors (Promega). Sequencing reactions were done using the Taq sequencing method.

(e) RACE Method

The RACE method (Rapid Amplification of cDNA Ends) was adapted from a published method (Frohman MA and Martin GR, In: *Technique—a Journal of Methods in Cell and Molecular Biology*, Vol. 1, No. 3, pp. 165–170 [1989]). Three nested gene-specific primers described in the above reference (GS-RT, GSo, and GSi) need to be designed for each gone to be amplified. The following conditions were used successfully for hPDE IV-C: In order to produce the 5' end of a hPDE IV cDNA, an RT reaction was performed on brainstem total RNA as above with the exception that the gene specific RT primer (GS-RT:5'-AGCCAGGTGATGATT-3') SEQ ID NO:10 was at a concentration of 0.1 pmol/µl. The reaction is incubated at 42° C. for 1 hour and then shifted to 52° C. for 30 min. (This higher temperature seemed to be critical to avoiding a premature truncation product in hPDE IV-B, presumably because of a sequence that RT has difficulty reading through, and this was adopted for hPDE IV-C as well.)

After removing buffers using a Centricon 30 filtration device and concentrating in a speedvac, one tails the cDNA with dATP using terminal transferase (TdT) in a 20 µl reaction volume. Final conditions are: 1×TdT buffer (40 mM potassium cacodylate pH 6.8, 0.1 mM dithiothreitol), 0.75 mM cobalt chloride ($CoCl_2$), 0.2 mM dATP, 1,250 U TdT/ ml. Incubate 37° C. for 5 min, inactivate TdT at 65° C. 5 min. This reaction is diluted with water to 500 µl and used as a template in a series of nested PCR reactions.

The first PCR amplification (50 µl) uses the same PCR buffer conditions as above, but uses three primers: the Primer/Adapter (Ro-Ri-dT$_{17}$ 5'-AAGCATCCGTCAGCATCGGCAGGACAAC(T$_{17}$)-3') SEQ ID NO:11 at 0.2 pmol/µl, the Forward Outside Primer (Ro: 5'-AAGCATCCGTCAGCATC-3') SEQ ID NO:12 at 0.5 pmol/µl, and the Gene-Specific Reverse Outside Primer (GSo: 5'-ACCGAGGCGTCGTTGTA-3') SEQ ID NO:13 at 0.5 pmol/µl. Taq polymerase is only added after denaturing the reaction to 95° C. for 5 min. and equilibrating to 72° C. For the first cycle, the annealing step is 10 min. at 55° C., and the extension is at 72° C. for 40 min. After that, cycling parameters (PE 9600 machine) are: Denature 94° C., 30 sec; Anneal 53° C., 30 sec; Polymerize 72° C., 45 sec. Amplify 28 cycles. Dilute this product 20× in water to serve as template for a second PCR reaction using primers nested just inside those used in the first PCR reaction. This greatly increases the specificity of the final PCR products.

The second 50 µl PCR reaction uses identical buffer conditions to the first, and uses 1 µl of the 20× diluted product from the first PCR reaction. The primers are the Forward Inside Primer (Ri: 5'-AGCATCGGCAGGACAAC-3') SEQ ID NO:14 and Gene-Specific Inside Primer (GSi: 5'-AAGAGGGCAGCCAGGAT-3') SEQ.ID. NO. 15), both at 0.5 pmol/µl. For 12 cycles, the parameters are the same as the final 28 cycles of the previous amplification. The annealing temperature is then raised to 60° C. for another 18 cycles. Products are then analyzed on an agarose gel, DNA fragments are gel isolated, subcloned into a convenient vector, and sequenced. DNA fragments should extend from the GSi primer to the 5' end of the mRNA(s). After obtaining a 5' sequence, this sequence is verified by re-amplifying it from cDNA (two independent PCR reactions) using unique primers designed from the sequence and resequencing the fragments obtained.

Sequence ID Summary 1. hPDE IV-C cDNA sequence. 2,091 bp.

2. Predicted amino acid sequence of hPDE IV-C. 481 amino acids.

3. Predicted amino acid sequence encoded by the hPDE IV-C expression vector pc3-hPDE IV-C. 506 amio acids.

I claim:

1. An isolated DNA fragment consisting of the DNA sequence of SEQ.ID.NO:1, or an allelic variant thereof.

2. A recombinant DNA fragment comprising the DNA fragment of claim 1.

3. A recombinant DNA vector comprising the recombimmt DNA fragment of claim 2.

4. A host cell comprising the recombinant DNA fragment of claim 2.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
( A ) LENGTH: 2091 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:1:

```
AGATCTCATG GTCACACAGG CACTCGGGGA ACAGATCTGG AACTTGGGTC CAGGAGTCCT      60

GGGTGGCCCC CGTGGGAACA GTTTCAGGGT CCAGATGAAG AGACGAAGTC GCGAGAGGCG     120

TGGGGTCCCT GAGCGGGGGG TTGGGCAGGC CCCTGACTGC CTCGGCTCCC AGAGGACACG     180

GGGCAGAAGC TGGCATTGGA GACGCTAGAC GAGCTGGACT GGTGCCTGGA TCAGTTGGAG     240

ACGCTGCAGA CCCGGCACTC GGTGGGGGAG ATGGCCTCCA ACAAGTTCAA GCGGATCCTG     300

AACCGGGAGT TGACCCACCT GTCCGAAACC AGCCGCTCCG GAACCAGGT GTCCGAGTAC      360

ATCTCCCGGA CCTTCCTGGA CCAGCAGACC GAGGTGGAGC TGCCCAAGGT GACCGCTGAG     420

GAGGCCCCAC AGCCCATGTC CCGGATCAGT GGCCTACATG GGCTCTGCCA CAGTGCCAGC     480

CTCTCCTCAG CCACTGTCCC ACGCTTTGGG GTCCAGACTG ACCAGGAGGA GCAACTGGCC     540

AAGGAGCTAG AAGACACCAA CAAGTGGGGA CTTGATGTGT TCAAGGTGGC GGAGCTAAGT     600

GGGAACCGGC CCCTCACAGC TATCATATTC AGCATTTTTC AGGAGCGGGA CCTGCTGAAG     660

ACATTCCAGA TCCCAGCAGA CACACTGGCC ACCTACCTGC TGATGCTGGA GGGTCACTAC     720

CACGCCAATG TGGCCTACCA CAACAGCCTA CATGCCGCCG ACGTGGCCCA GTCCACGCAT     780

GTGCTGCTGG CTACGCCGGC CCTCGAGGCT GTGTTCACAG ACTTGGAAAT CCTGGCTGCC     840

CTCTTTGCAA GCGCCATCCA CGACGTGGAC CATCCTGGGG TCTCCAACCA GTTTCTGATT     900
```

-continued

| | | | | | |
|---|---|---|---|---|---|
| AACACCAACT | CAGAGCTGGC | GCTTATGTAC | AACGACGCCT | CGGTGCTGGA | GAATCATCAC | 960
| CTGGCTGTGG | GCTTCAAGCT | GCTGCAGGCA | GAGAACTGCG | ATATCTTCCA | GAACCTCAGC | 1020
| GCCAAGCAGC | GACTGAGTCT | GCGCAGGATG | GTCATTGACA | TGGTGCTGGC | CACAGACATG | 1080
| TCCAAACACA | TGAACCTCCT | GGCCGACCTC | AAGACCATGG | TGGAGACCAA | GAAGGTGACA | 1140
| AGCCTCGGTG | TCCTCCTCCT | GGACAACTAT | TCCGACCGAA | TCCAGGTCTT | GCAGAACCTG | 1200
| GTGCACTGTG | CTGATCTGAG | CAACCCCACC | AAGCCGCTGC | CCTGTACCG | CCAGTGGACG | 1260
| GACCGCATCA | TGGCCGAGTT | CTTCCAGCAG | GGAGACCGCG | AGCGTGAGTC | GGGCCTGGAC | 1320
| ATCAGTCCCA | TGTGTGACAA | GCATACGGCC | TCAGTGGAGA | AGTCCCAGGT | GGGTTTCATT | 1380
| GACTACATTG | CTCACCCACT | GTGGGAGACT | GGGCTGACC | TGGTCCACCC | AGATGCACAG | 1440
| GACCTGCTGG | ACACGCTGGA | GGACAATCGA | GAGTGGTACC | AGAGCAAGAT | CCCCCGAAGT | 1500
| CCCTCAGACC | TCACCAACCC | CGAGCGGGAC | GGGCCTGACA | GATTCCAGTT | TGAACTGACT | 1560
| CTGGAGGAGG | CAGAGGAAGA | GGATGAGGAG | GAAGAAGAGG | AGGGGAAGA | GACAGCTTTA | 1620
| GCCAAAGAGG | CCTTGGAGTT | GCCTGACACT | GAACTCCTGT | CCCCTGAAGC | CGGCCCAGAC | 1680
| CCTGGGGACT | TACCCCTCGA | CAACCAGAGG | ACTTAGGGCC | AGCCCTGCGT | GAACTGCAGG | 1740
| GCCAATGGAT | GGTAAAGCCC | TTTGGCTCTT | GGCAGGCAGA | CTTTCCAGGA | AGAGGCTCCA | 1800
| TGTGGCTCCT | GCTTCACTTT | CCCACCCATT | TAGGGAGACA | ATCAAGCTCT | TAGTTATAGG | 1860
| TGGCTCCCAG | GGTCTAATTG | GAGGCACCTG | GCTGGGGTCC | ACTCTGACCC | TAGACTTGCC | 1920
| TAAAAGAGCT | CTCTAAGGGG | CAGCCTCTTA | CGATGCCCTG | GTGTCTTTCT | CCTGGGCTTC | 1980
| TATCCCTGTG | AGGAGAGGTG | CTGTCTGCTG | GAGCCTCTAG | TCCACCCTCT | CCAGTGGTCA | 2040
| CTCTTGAGTC | ACATCTGTCA | CTTAATTATT | TCCTTCTTTA | TCAAATATTT | A | 2091

(2) INFORMATION FOR SEQ ID NO:2:

(i) SEQUENCE CHARACTERISTICS:
    (A) LENGTH: 481 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:2:

```
Met  Ala  Ser  Asn  Lys  Phe  Lys  Arg  Ile  Leu  Asn  Arg  Glu  Leu  Thr  His
  1                5                    10                       15

Leu  Ser  Glu  Thr  Ser  Arg  Ser  Gly  Asn  Gln  Val  Ser  Glu  Tyr  Ile  Ser
                20                   25                       30

Arg  Thr  Phe  Leu  Asp  Gln  Gln  Thr  Glu  Val  Glu  Leu  Pro  Lys  Val  Thr
           35                   40                       45

Ala  Glu  Glu  Ala  Pro  Gln  Pro  Met  Ser  Arg  Ile  Ser  Gly  Leu  His  Gly
     50                   55                       60

Leu  Cys  His  Ser  Ala  Ser  Leu  Ser  Ser  Ala  Thr  Val  Pro  Arg  Phe  Gly
 65                        70                       75                        80

Val  Gln  Thr  Asp  Gln  Glu  Glu  Gln  Leu  Ala  Lys  Glu  Leu  Glu  Asp  Thr
                     85                       90                       95

Asn  Lys  Trp  Gly  Leu  Asp  Val  Phe  Lys  Val  Ala  Glu  Leu  Ser  Gly  Asn
               100                      105                      110

Arg  Pro  Leu  Thr  Ala  Ile  Ile  Phe  Ser  Ile  Phe  Gln  Glu  Arg  Asp  Leu
          115                      120                      125

Leu  Lys  Thr  Phe  Gln  Ile  Pro  Ala  Asp  Thr  Leu  Ala  Thr  Tyr  Leu  Leu
     130                      135                      140
```

| | | | | | | | | | | | | | | | |
|---|---|---|---|---|---|---|---|---|---|---|---|---|---|---|---|
|Met|Leu|Glu|Gly|His|Tyr|His|Ala|Asn|Val|Ala|Tyr|His|Asn|Ser|Leu|
|145| | | | |150| | | | |155| | | | |160|
|His|Ala|Ala|Asp|Val|Ala|Gln|Ser|Thr|His|Val|Leu|Leu|Ala|Thr|Pro|
| | | | |165| | | | |170| | | | |175| |
|Ala|Leu|Glu|Ala|Val|Phe|Thr|Asp|Leu|Glu|Ile|Leu|Ala|Ala|Leu|Phe|
| | | | |180| | | | |185| | | | |190| |
|Ala|Ser|Ala|Ile|His|Asp|Val|Asp|His|Pro|Gly|Val|Ser|Asn|Gln|Phe|
| | | |195| | | | |200| | | | |205| | |
|Leu|Ile|Asn|Thr|Asn|Ser|Glu|Leu|Ala|Leu|Met|Tyr|Asn|Asp|Ala|Ser|
| | | |210| | | | |215| | | | |220| | | |
|Val|Leu|Glu|Asn|His|His|Leu|Ala|Val|Gly|Phe|Lys|Leu|Leu|Gln|Ala|
|225| | | | |230| | | | |235| | | | |240|
|Glu|Asn|Cys|Asp|Ile|Phe|Gln|Asn|Leu|Ser|Ala|Lys|Gln|Arg|Leu|Ser|
| | | | |245| | | | |250| | | | |255| |
|Leu|Arg|Arg|Met|Val|Ile|Asp|Met|Val|Leu|Ala|Thr|Asp|Met|Ser|Lys|
| | | |260| | | | |265| | | | |270| | |
|His|Met|Asn|Leu|Leu|Ala|Asp|Leu|Lys|Thr|Met|Val|Glu|Thr|Lys|Lys|
| | |275| | | | |280| | | | |285| | | |
|Val|Thr|Ser|Leu|Gly|Val|Leu|Leu|Leu|Asp|Asn|Tyr|Ser|Asp|Arg|Ile|
|290| | | | |295| | | | |300| | | | | |
|Gln|Val|Leu|Gln|Asn|Leu|Val|His|Cys|Ala|Asp|Leu|Ser|Asn|Pro|Thr|
|305| | | | |310| | | | |315| | | | |320|
|Lys|Pro|Leu|Pro|Leu|Tyr|Arg|Gln|Trp|Thr|Asp|Arg|Ile|Met|Ala|Glu|
| | | | |325| | | | |330| | | | |335| |
|Phe|Phe|Gln|Gln|Gly|Asp|Arg|Glu|Arg|Glu|Ser|Gly|Leu|Asp|Ile|Ser|
| | | |340| | | | |345| | | | |350| | |
|Pro|Met|Cys|Asp|Lys|His|Thr|Ala|Ser|Val|Glu|Lys|Ser|Gln|Val|Gly|
| | |355| | | | |360| | | | |365| | | |
|Phe|Ile|Asp|Tyr|Ile|Ala|His|Pro|Leu|Trp|Glu|Thr|Trp|Ala|Asp|Leu|
| | |370| | | | |375| | | | |380| | | |
|Val|His|Pro|Asp|Ala|Gln|Asp|Leu|Leu|Asp|Thr|Leu|Glu|Asp|Asn|Arg|
|385| | | | |390| | | | |395| | | | |400|
|Glu|Trp|Tyr|Gln|Ser|Lys|Ile|Pro|Arg|Ser|Pro|Ser|Asp|Leu|Thr|Asn|
| | | | |405| | | | |410| | | | |415| |
|Pro|Glu|Arg|Asp|Gly|Pro|Asp|Arg|Phe|Gln|Phe|Glu|Leu|Thr|Leu|Glu|
| | | |420| | | | |425| | | | |430| | |
|Glu|Ala|Glu|Glu|Glu|Asp|Glu|Glu|Glu|Glu|Glu|Gly|Glu|Glu|Thr|
| | |435| | | | |440| | | | |445| | | |
|Ala|Leu|Ala|Lys|Glu|Ala|Leu|Glu|Leu|Pro|Asp|Thr|Glu|Leu|Leu|Ser|
| |450| | | | |455| | | | |460| | | | |
|Pro|Glu|Ala|Gly|Pro|Asp|Pro|Gly|Asp|Leu|Pro|Leu|Asp|Asn|Gln|Arg|
|465| | | | |470| | | | |475| | | | |480|
|Thr| | | | | | | | | | | | | | | |

( 2 ) INFORMATION FOR SEQ ID NO:3:

( i ) SEQUENCE CHARACTERISTICS:
        ( A ) LENGTH: 506 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

Met Val Pro Leu Asp Glu Leu Asp Trp Cys Leu Asp Gln Leu Glu Thr

-continued

| 1 | | | | 5 | | | | | 10 | | | | | 15 |
|---|---|---|---|---|---|---|---|---|---|---|---|---|---|---|
| Leu | Gln | Thr | Arg<br>20 | His | Ser | Val | Gly | Glu<br>25 | Met | Ala | Ser | Asn<br>30 | Lys | Phe | Lys |
| Arg | Ile | Leu<br>35 | Asn | Arg | Glu | Leu | Thr<br>40 | His | Leu | Ser | Glu | Thr<br>45 | Ser | Arg | Ser |
| Gly | Asn<br>50 | Gln | Val | Ser | Glu | Tyr<br>55 | Ile | Ser | Arg | Thr | Phe<br>60 | Leu | Asp | Gln | Gln |
| Thr<br>65 | Glu | Val | Glu | Leu | Pro<br>70 | Lys | Val | Thr | Ala | Glu<br>75 | Glu | Ala | Pro | Gln | Pro<br>80 |
| Met | Ser | Arg | Ile | Ser<br>85 | Gly | Leu | His | Gly<br>90 | Leu | Cys | His | Ser | Ala<br>95 | Ser | Leu |
| Ser | Ser | Ala | Thr<br>100 | Val | Pro | Arg | Phe | Gly<br>105 | Val | Gln | Thr | Asp | Gln<br>110 | Glu | Glu |
| Gln | Leu | Ala<br>115 | Lys | Glu | Leu | Glu | Asp<br>120 | Thr | Asn | Lys | Trp | Gly<br>125 | Leu | Asp | Val |
| Phe | Lys<br>130 | Val | Ala | Glu | Leu | Ser<br>135 | Gly | Asn | Arg | Pro | Leu<br>140 | Thr | Ala | Ile | Ile |
| Phe<br>145 | Ser | Ile | Phe | Gln | Glu<br>150 | Arg | Asp | Leu | Leu | Lys<br>155 | Thr | Phe | Gln | Ile | Pro<br>160 |
| Ala | Asp | Thr | Leu | Ala<br>165 | Thr | Tyr | Leu | Leu | Met<br>170 | Leu | Glu | Gly | His | Tyr<br>175 | His |
| Ala | Asn | Val | Ala<br>180 | Tyr | His | Asn | Ser | Leu<br>185 | His | Ala | Ala | Asp | Val<br>190 | Ala | Gln |
| Ser | Thr | His<br>195 | Val | Leu | Leu | Ala | Thr<br>200 | Pro | Ala | Leu | Glu | Ala<br>205 | Val | Phe | Thr |
| Asp | Leu<br>210 | Glu | Ile | Leu | Ala | Ala<br>215 | Leu | Phe | Ala | Ser | Ala<br>220 | Ile | His | Asp | Val |
| Asp<br>225 | His | Pro | Gly | Val | Ser<br>230 | Asn | Gln | Phe | Leu | Ile<br>235 | Asn | Thr | Asn | Ser | Glu<br>240 |
| Leu | Ala | Leu | Met | Tyr<br>245 | Asn | Asp | Ala | Ser | Val<br>250 | Leu | Glu | Asn | His | His<br>255 | Leu |
| Ala | Val | Gly | Phe<br>260 | Lys | Leu | Leu | Gln | Ala<br>265 | Glu | Asn | Cys | Asp | Ile<br>270 | Phe | Gln |
| Asn | Leu | Ser<br>275 | Ala | Lys | Gln | Arg | Leu<br>280 | Ser | Leu | Arg | Arg | Met<br>285 | Val | Ile | Asp |
| Met | Val<br>290 | Leu | Ala | Thr | Asp | Met<br>295 | Ser | Lys | His | Met | Asn<br>300 | Leu | Leu | Ala | Asp |
| Leu<br>305 | Lys | Thr | Met | Val | Glu<br>310 | Thr | Lys | Lys | Val | Thr<br>315 | Ser | Leu | Gly | Val | Leu<br>320 |
| Leu | Leu | Asp | Asn | Tyr<br>325 | Ser | Asp | Arg | Ile | Gln<br>330 | Val | Leu | Gln | Asn | Leu<br>335 | Val |
| His | Cys | Ala | Asp<br>340 | Leu | Ser | Asn | Pro | Thr<br>345 | Lys | Pro | Leu | Pro | Leu<br>350 | Tyr | Arg |
| Gln | Trp | Thr<br>355 | Asp | Arg | Ile | Met | Ala<br>360 | Glu | Phe | Phe | Gln | Gln<br>365 | Gly | Asp | Arg |
| Glu | Arg<br>370 | Glu | Ser | Gly | Leu | Asp<br>375 | Ile | Ser | Pro | Met | Cys<br>380 | Asp | Lys | His | Thr |
| Ala<br>385 | Ser | Val | Glu | Lys | Ser<br>390 | Gln | Val | Gly | Phe | Ile<br>395 | Asp | Tyr | Ile | Ala | His<br>400 |
| Pro | Leu | Trp | Glu | Thr<br>405 | Trp | Ala | Asp | Leu | Val<br>410 | His | Pro | Asp | Ala | Gln<br>415 | Asp |
| Leu | Leu | Asp | Thr<br>420 | Leu | Glu | Asp | Asn | Arg<br>425 | Glu | Trp | Tyr | Gln | Ser<br>430 | Lys | Ile |

```
Pro Arg Ser Pro Ser Asp Leu Thr Asn Pro Glu Arg Asp Gly Pro Asp
        435             440             445

Arg Phe Gln Phe Glu Leu Thr Leu Glu Glu Ala Glu Glu Asp Glu
    450             455             460

Glu Glu Glu Glu Glu Gly Glu Glu Thr Ala Leu Ala Lys Glu Ala Leu
465             470             475             480

Glu Leu Pro Asp Thr Glu Leu Leu Ser Pro Glu Ala Gly Pro Asp Pro
            485             490             495

Gly Asp Leu Pro Leu Asp Asn Gln Arg Thr
            500             505
```

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

GGAGAAGTCC CAGGTGGGTT T                        21

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

TCTGGTTGTC GAGGGGTAAG T                        21

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

CGAAGAAAGT TACAAGTTCA                         20

( 2 ) INFORMATION FOR SEQ ID NO:7:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

AACCTGGGAT TTTTCCACA                          19

( 2 ) INFORMATION FOR SEQ ID NO:8:

( i ) SEQUENCE CHARACTERISTICS:
        ( A ) LENGTH: 19 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:8:

CACCTGCATC ATGTACATG 19

(2) INFORMATION FOR SEQ ID NO:9:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:9:

TCCCGGTTGT CCTCCAAAG 19

(2) INFORMATION FOR SEQ ID NO:10:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:10:

AGCCAGGTGA TGATT 15

(2) INFORMATION FOR SEQ ID NO:11:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:11:

AAGCATCCGT CAGCATCGGC AGGACAACTT TTTTTTTTT TTTTT 45

(2) INFORMATION FOR SEQ ID NO:12:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:12:

AAGCATCCGT CAGCATC 17

(2) INFORMATION FOR SEQ ID NO:13:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: cDNA ( x i ) SEQUENCE DESCRIPTION: SEQ ID NO:13:

ACCGAGGCGT CGTTGTA                                                               17

( 2 ) INFORMATION FOR SEQ ID NO:14:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

AGCATCGGCA GGACAAC                                                               17

( 2 ) INFORMATION FOR SEQ ID NO:15:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

AAGAGGGCAG CCAGGAT                                                               17